United States Patent [19]
Douglas-Hamilton et al.

[11] Patent Number: 5,306,467
[45] Date of Patent: Apr. 26, 1994

[54] APPARATUS FOR MEASUREMENT OF CELL CONCENTRATION IN A BIOLOGICAL SAMPLE EMPLOYING A MAGNETIC SLIDE LOADING APPARATUS

[75] Inventors: Diarmaid H. Douglas-Hamilton, Beverly; Thomas Kenny, Woburn, both of Mass.

[73] Assignee: Hamilton-Thorn Research, Beverly, Mass.

[21] Appl. No.: 18,734

[22] Filed: Feb. 17, 1993

[51] Int. Cl.$^5$ .......................... B01L 3/00; B01L 9/00; G01N 21/01
[52] U.S. Cl. .......................... 422/99; 422/104; 211/DIG. 1; 248/206.5; 356/244; 359/391; 359/398; 359/903
[58] Field of Search .............. 422/99, 104; 356/244, 356/246; 359/391, 398, 903; 248/206.5; 211/DIG. 1

[56] References Cited

U.S. PATENT DOCUMENTS

| | | | |
|---|---|---|---|
| 1,230,740 | 6/1917 | McCracken | 211/DIG. 1 X |
| 1,864,788 | 6/1932 | Batchelder | 211/DIG. 1 X |
| 1,882,919 | 10/1932 | Robbins | 359/391 |
| 2,152,897 | 4/1939 | Madore | 211/DIG. 1 X |
| 2,164,623 | 7/1939 | Posner | 211/DIG. 1 X |
| 2,527,482 | 10/1950 | Kinzler et al. | 248/206.5 X |
| 2,580,099 | 12/1951 | Jaeger | 248/206.5 X |
| 2,781,692 | 2/1959 | Krause | 359/391 |
| 2,890,848 | 6/1959 | Johnson, Jr. | 248/206.5 X |
| 3,588,259 | 6/1971 | Harvey | 356/244 |
| 3,848,963 | 11/1974 | Peck | 359/391 |
| 3,879,106 | 4/1976 | McCormick | 359/398 |
| 4,022,521 | 5/1977 | Hall et al. | 356/244 X |
| 4,222,489 | 9/1980 | Hutter | 211/DIG. 1 X |
| 4,407,570 | 10/1983 | Hayasaka | 359/391 |
| 4,501,495 | 2/1985 | Faulkner et al. | 356/244 |
| 4,556,297 | 12/1985 | Schulz, Jr. | 359/391 X |
| 4,605,292 | 8/1986 | McIntosh | 359/903 X |
| 4,911,782 | 3/1990 | Brown | 156/633 |
| 4,946,266 | 8/1990 | Kraft et al. | 359/391 |
| 4,971,278 | 11/1990 | Woods | 248/206.5 |

FOREIGN PATENT DOCUMENTS 2821002 11/1979 Fed. Rep. of Germany ...... 359/903

OTHER PUBLICATIONS

Cell-VU TM Brochure, 1993, Fertility Technologies, Inc., 313 Speen Street, Natick, Mass. 01760.
Hemacytometer, Fisher Scientific Catalog, 1993, Fisher Scientic, Inc., 50 Fadem Road, Springfield, N.J. 07081-3193.
Makler Counting Chamber publication, 1992, Sefi Medical Instruments Ltd., Haifa, Israel.
Abstract of "Operating Characteristics of a New Semen Analysis Chamber", given at The American Fertility Society, submitted Mar. 1, 1989.

Primary Examiner—James C. Housel
Assistant Examiner—Milton I. Cano
Attorney, Agent, or Firm—Lahive & Cockfield

[57] ABSTRACT

A magnetic slide loading is used with automated cell counting equipment or manual optical microscopes to measure the number of cells in a fluid biological sample. A slide having a defined volume region holds the sample for measurement. A cover slip is placed over the defined volume region creating an enclosed volume. An actuable holder clamp is placed over the slide securing it as well as the cover slip in position by virtue of magnets secured to the bottom of the device exerting a magnetic force upon the holder clamp such that it is attracted toward the slide forcing the cover slip to flatten, thereby removing any defects or distortions from the volume. This action ensures that the volume has a uniform depth allowing accurate measurement of cell concentration within the biological sample.

8 Claims, 3 Drawing Sheets

APPARATUS FOR MEASUREMENT OF CELL CONCENTRATION IN A BIOLOGICAL SAMPLE EMPLOYING A MAGNETIC SLIDE LOADING APPARATUS

BACKGROUND OF THE INVENTION

This invention relates, in general, to slide loading devices for use in automated cell counting systems or standard optical microscopes. More particularly, the invention relates to a slide holder that exerts a uniform force on a coverslip ensuring a uniform volume of a sample on the slide.

Accurate measurement of cell concentration in a biological sample is important in a variety of medical fields. For example, the concentration of leukocytes in blood or sperm cells in semen serve as diagnostic indicators. In particular the concentration of sperm cells is a direct indicator of fertility. In this situation the concentration may vary from zero to more than 100 million cells per milliliter. In response to the need for accurate measurement, a variety of devices have been proposed or developed for measuring cell concentration.

One type of apparatus for measuring the concentration of cells is a flow cytometer in which cells are individually counted as they emerge in a stream from an orifice. Knowing the flow rate allows the technician to calculate the cell concentration. Due to the size of the orifice which is necessary to govern low, the orifice is subject to blockage and other problems, requiring highly skilled operation and care of this expensive and delicate device.

An alternative method has been used to measure the concentration which involves measuring the area density of cells in a preparation of known depth. A chamber is defined by grid lines drawn in squares and has a known depth (usually 10-1000 $\mu$m). Knowing the chamber depth and counting the number of cells per unit area in the grid gives the concentration. The accuracy of this measurement is proportional to the accuracy with which the chamber depth is known.

Various apparatus configurations have been devised to accommodate this method. The Hemacytometer uses a glass coverslip suspended over a specimen plate, the gap being filled by capillary action. This system uses a chamber depth of approximately 100 $\mu$m which is too large for highly concentrated fluids such as semen. Additionally, to count such fluids with motile cells, a lethal diluent must be used to immobilize the cells. This, naturally, prevents the observation of the moving cells. Because the 100 $\mu$m chamber depth is greater than the focal depth of the typical objective lens system employed, a smaller chamber depth is required.

Another device that uses the above method is the Makler chamber. This device has a weighted coverslip suspended on four posts approximately 10 $\mu$m above the specimen plate. The weight of the coverslip forces the specimen to spread out to a depth of 10 $\mu$m. Using this device can result in considerable over-estimations of concentration because the viscosity of the fluid specimen impacts the fluid's ability to spread. Also, if a solid particle should become lodged under the coverslip, the depth is affected, again skewing the measurement.

A third device that uses the above method is the Microcell. It uses two fixed planes of glass to achieve a separation distance of 20 $\mu$m and is filled by capillary action. Since the distance between the planes can be measured, the chamber depth is known. In this device, viscous samples are unable to fill the chamber by capillary action. Also, since precise measurement of the separation distance between the two glass planes is required to know the chamber depth, the preparation of the device is expensive. Capillary action further risks damaging fragile cells such as sperm due to the fluid flow causing a tumbling motion during loading.

A simpler alternative was developed which uses a printed ink pattern on a slide to define an area of constant depth. Placing a coverslip over it provides a chamber of known depth permitting concentration to be measured. This alternative overcomes most of the aforementioned problems, but introduces another. Unless the coverslip is maintained at the correct distance from the slide, the chamber distance will not be constant between samples. Too much sample will cause the coverslip to rise, while too little will distort the slip inwardly through capillary action. Any such distortion, at a 20 $\mu$m depth, is significant enough to give erroneous results.

Accordingly, there exists a need for a slide loading device which can provide accurate and reliable measurement and observation of a biological sample, regardless of the viscosity of the fluid.

It is another object of the invention to provide a slide loading device which yields accurate measurement of cell concentration, independently of the amount of sample in the chamber.

Other general and specific objects of the invention will in part be obvious and will in part appear hereinafter.

SUMMARY OF THE INVENTION

Broadly speaking, the present invention provides apparatus for measuring cell concentration in a biological specimen. This is achieved by applying a uniform pressure on the edges of a coverslip overlying a specimen volume defined by an "O" shaped ring or other specimen chamber of known depth on a slide, such that the coverslip is firmly and uniformly held in place on the defined volume. This pressure forces the coverslip to be planar without substantial fluctuations in topography.

This apparatus is, then, designed for use with a slide which has a defined volume on its surface, for example by a rim of known depth adhered to the slide and open on top. The volume may be circular, an 'O' shape, or it may be open, with side walls forming an area of a known height. The fluid specimen is placed within this volume on the slide and is covered by a coverslip. Placing the fluid specimen within the volume of known depth allows accurate measurement of cell concentration if the top surface, made by the coverslip, is flat and uniform.

The slide and cover slip assembly is placed into a slide loading apparatus. The slide loading apparatus comprises a slide holder which has a recess in its surface where the slide holding the specimen is placed. Within the surface area enclosed by this recess is an aperture which allows light to pass through the holder to illuminate the slide during examination of the specimen.

The slide is then secured to the holder by a holder clamp which may, for example, be hinged to the holder. The holder clamp is formed of magnetically susceptible material and also has an opening over the defined volume and the aperture in the holder to allow examination of the specimen.

Embedded into the bottom of the slide holder are magnets. The magnets produce an attractive force on the holder clamp. The holder clamp, already in mechanical contact with the coverslip, now, under the influence of the magnetic field, bears sufficiently uniformly on the coverslip to remove any remaining imperfections in the surface.

The coverslip, being pressed down flat, is compressed against the top of the enclosed volume. Excess fluid in the volume is forced out, leaving a sample of uniform depth within the volume between the coverslip and the slide. With a known volume filled to a uniform depth, the cell concentration may now be easily calculated with accuracy.

An alternative embodiment allows the use of smaller magnets in the slide holder by using magnetic strips on the holder clamp. By doing so, the thickness of the slide holder and the width of the holder clamp's legs can be reduced to produce a holder more amenable to manual microscopy.

The invention accordingly comprises the several steps and relation of one or more of steps with respect to each of the others, and the apparatus embodying features of construction, combinations of elements and arrangements of parts adapted to affect following detailed description, and the scope of the invention is indicated in the claims.

BRIEF DESCRIPTION OF THE DRAWINGS

For a fuller understanding of the nature and objects of the invention, reference should be made to the following detailed description and the accompanying drawings, in which.

DESCRIPTION OF THE PREFERRED EMBODIMENT

The invention, in one aspect, provides a slide loading apparatus which ensures a consistently uniform separation distance between a coverslip and a slide so that a cell concentration in a biological fluid specimen may be measured accurately.

A slide having a defined region filled with a specimen is placed in the apparatus for cell counting. The defined region is generally an '0' shaped rim deposited onto the slide surface with a known depth of approximately 20 μm. By knowing the depth and having the surface of the region capped at a height consistent with the height of the side of the region, concentration may easily be calculated.

Figure 1:
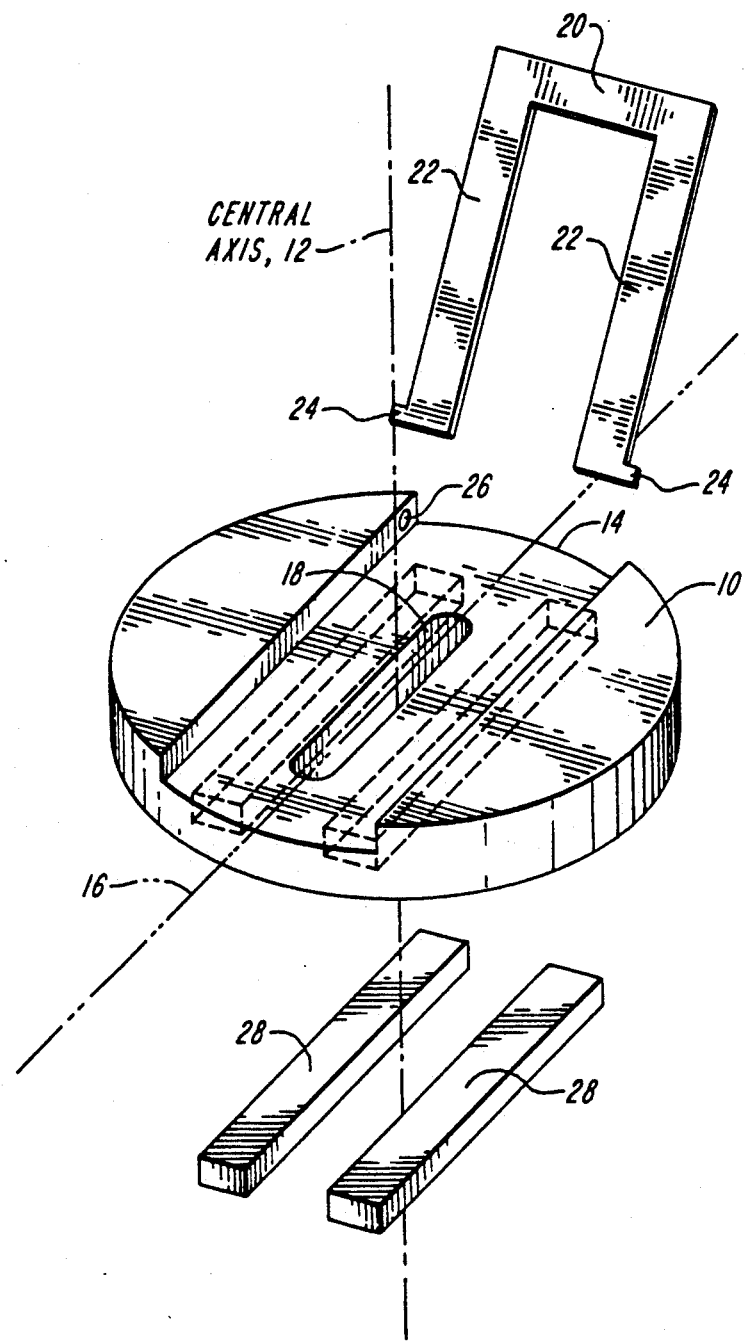
FIG. 1 is an exploded view of a slide holder according to the invention.

A slide loading apparatus according to the invention, as shown in FIG. 1, has a slide holder 10. The slide holder may be disk-shaped or rectangular with the central axis 12 of the system passing through the center of the disk on an axis normal to the plane of the disk.

Figure 2:
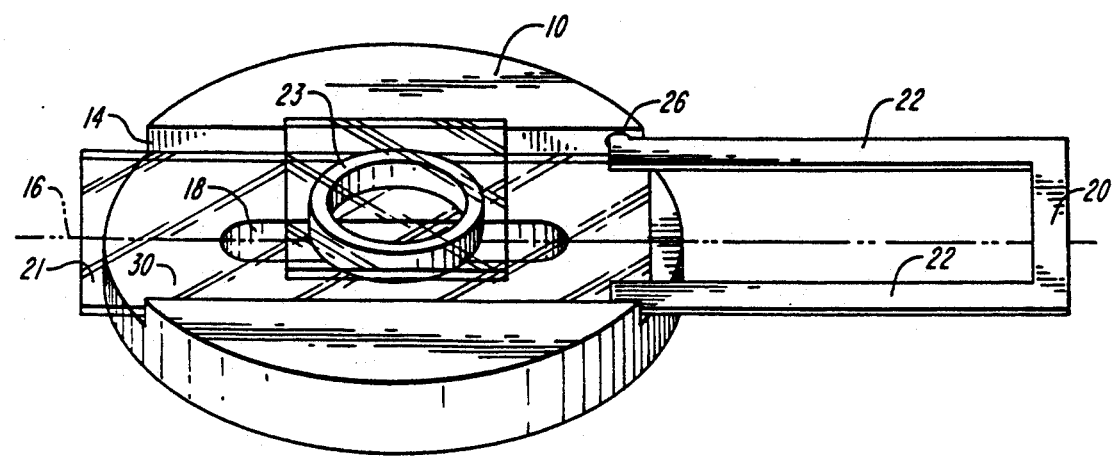
FIG. 2 is a top perspective view of a slide holder according to the system of FIG. 1 with the holder clamp in an opened position and with a slide held within.

The slide holder 10 is fabricated with a recess extending across a diameter of the slide holder. The diameter forms a transverse axis 16 perpendicular to the central axis 12. As shown in FIG. 2, the recess extends approximately equidistantly lateral to the transverse axis for a distance long enough to accommodate a slide 21. In the preferred embodiment, the width of recess 14 is 2.6 centimeters. Likewise, the depth is such that the slide can be fully encompassed therein, approximately 0.5 centimeters.

Figure 2A:
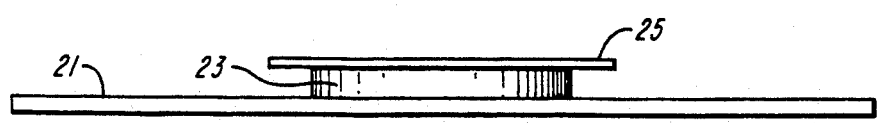
FIG. 2A is an elevational view of a typical slide used with the system of FIG. 1.

A slide useful for the purpose of containing a liquid sample in a known volume is formed, as illustrated in FIG. 2 and 2A with an "O" shaped rim 23 deposited in a sealed fashion on the upper surface of the slide 21. The slide conventionally has a coverslip 25 found of a thin flat layer of glass covering the volume found by the rim 23.

An aperture 18 in holder 10 extends along the transverse axis 16 to allow light, or other forms of radiation, to pass through the slide holder 10 with minimal impedance. In the preferred embodiment, the aperture 18 has an oval shape and its center point falls on the central axis 12.

Embedded into the underside of the slide holder 10 are bar magnets 28. These magnets are magnetized in a direction normal to their long axis generating a magnetic force approximately parallel to the central axis 12. The magnets are secured to the slide holder 10 in appropriately sized depressions in the bottom by an adhesive, such as epoxy.

A holder clamp 20 couples to the slide holder 10 for retaining a slide 21 and coverslip 23 in position within the recess 14. In the preferred embodiment, the holder clamp 20 is U-shaped to allow radiation to pass through the aperture 18 and between the legs 22 of clamp 20 without hindrance.

In the preferred embodiment, the holder clamp 20 is pivotally mounted on slide holder 10, although other methods of attachment are available. The pivoted coupling is achieved by inserting lateral extensions 24 off the legs 22 into bores in the recess walls.

In this embodiment, the holder clamp 20 is constructed from a magnetically susceptible material, for example, steel, iron, stainless steel, spring steel, or other ferromagnetic material. The clamp 20 may also have a layer of plastic or rubber on its underside to provide better conformal uniform pressure on the coverslip.

FIG. 2 shows the assembled apparatus with the holder clamp 20 in an open position, with slide 21 in position. FIG. 2A illustrates in elevational view the relative position of the slide 21, rim 23 and coverslip 25.

Once a slide is placed into the recess 14, the holder clamp 20 is rotated to lock the slide and coverslip into place. When the rotation is completed the coverslip 25 is flattened against rim 23 and locked into position.

The bar magnets 28 generate a magnetic force up through the slide attracting the holder clamp thereby producing uniform pressure on the cover slip 25 which is sufficient to smooth any remaining defects in the coverslip.

As the coverslip 25 is placed over a fluid sample within a defined volume, the portion of the coverslip which forms the top of the volume is flattened by the additional pressure on the holder clamp 20. This action forces overflow of excess fluid sample leaving only an amount which can fit in to the defined volume of uniform depth.

In the embodiment of FIG. 2, the slide holder 10 is straight along one edge of its disk shape. This edge is a chord 30 of the circle formed by the face of the disk.

This shape allows ease of actuation of the holder clamp 20 by leaving part of the holder clamp 20 extending past the chord 30.

Figure 3:
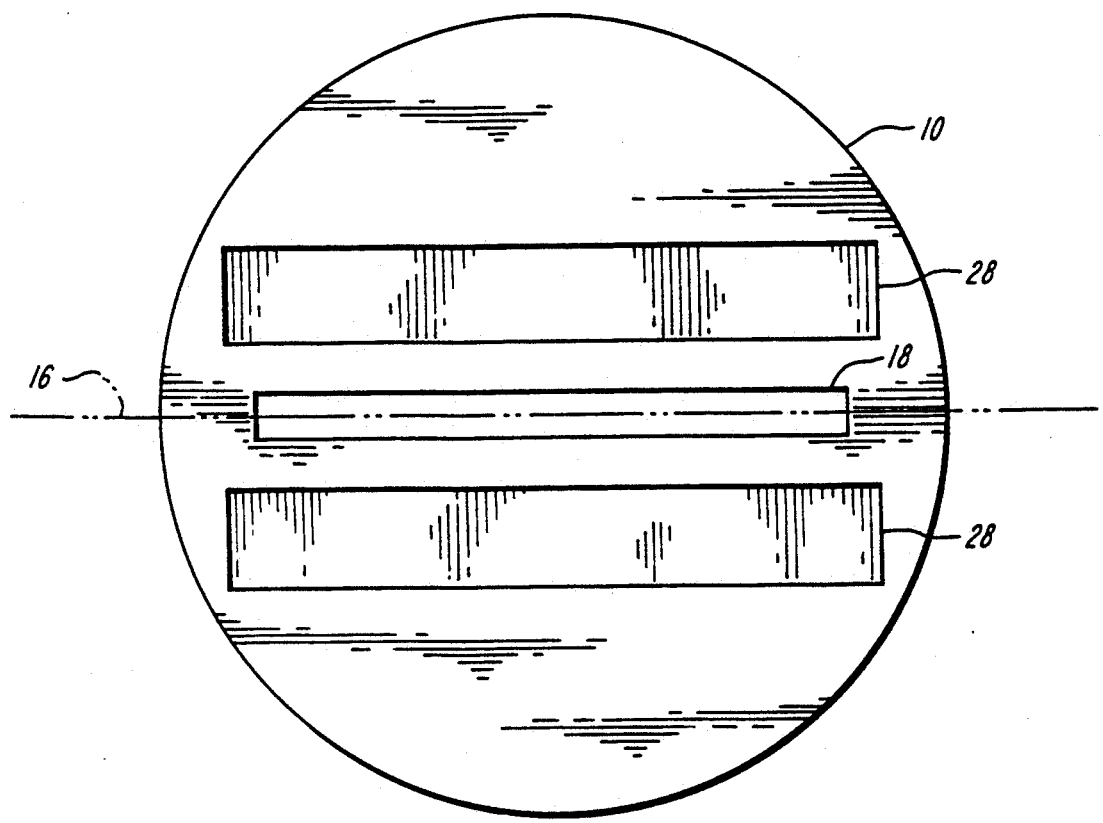
FIG. 3 is a bottom view of the slide holder according to the system of FIG. 1.

FIG. 3 shows a view of the apparatus from the bottom. This view better illustrates the positioning of the bar magnets 28 with respect to the aperture 18.

In an alternative embodiment which is more conducive to use with manual microscopy, it becomes more important that the specimen is as close to the microscope condenser as possible in order to maintain the use of the full range of available illumination optics. Therefore, the aperture 18 is widened to allow passage of more light and, likewise, the legs 22 of the holder clamp 20 are narrowed to accommodate the widened aperture. For manual microscopy a rectangular shape to the slide holder 10 may be more convenient with the long axis of the rectangle parallel to the slide length.

Figure 4:
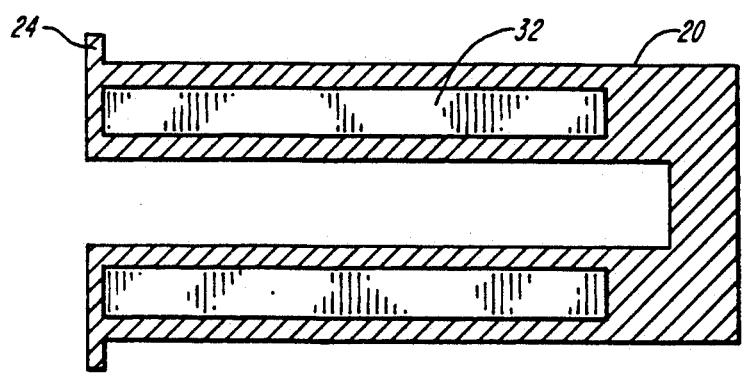
FIG. 4 is an alternative embodiment of a holder clamp according to the system of FIG. 1.

Since the legs 22 of the holder clamp 20 are narrowed, the bar magnets 28 can no longer achieve the same attractive force that they could in the embodiment previously described because of the decreased surface area. Therefore, magnetic strips 32 of opposite Polarity to that of the bar magnets 28 may be placed on the top of the holder clamp 20 as shown in FIG. 4. The holder clamp 20 may now be fabricated from non-magnetically susceptible material, such as delrin, nylon or PVC, with a plastic or rubber base to aid conformal fitting to the slide.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

What is claimed is:

1. A slide loading apparatus for receiving a slide holding a fluid specimen within a defined region of uniform depth, said specimen being covered by a cover slip, said apparatus comprising,
   a holder having a recess for receiving said slide, and an aperture for allowing radiation to pass there through,
   a holder clamp formed to include magnetically susceptible material, pivotally secured to said holder wherein said holder clamp can be placed in mechanical contact with said cover slip, said holder clamp having an opening therethrough aligned with said aperture in said holder when said holder clamp is in mechanical contact with said cover slip, and
   first magnetic means coupled to said holder, for applying a uniform magnetic attraction to said holder clamp such that, when placed in mechanical contact with said cover slip, said holder clamp exerts a uniform pressure on said cover slip to maintain a constant separation distance between said slide and said cover slip over said defined region.

2. The apparatus according to claim 1 wherein said holder clamp is generally U-shaped.

3. The apparatus according to claim 2 wherein said holder clamp further comprises, multiple projections at a cross-connection portion of said U-shape, which projections are received by bores in said slide holder allowing said holder clamp pivotal motion with respect to said holder.

4. The apparatus according to claim 1 having a layer of resilient material attached to said holder clamp for making contact with said cover slip.

5. A slide holding apparatus for receiving a slide holding a fluid specimen within a defined volume of uniform depth, said specimen being covered by a cover slip, said apparatus comprising,
   a holder having a recess for receiving said slide, and an aperture for allowing radiation to pass therethrough,
   a holder clamp mechanically and pivotally secured to said holder, wherein said holder clamp can be placed in mechanical contact with said cover slip, said holder clamp having a profile to permit conformal superimposition of said holder clamp onto the slide,
   a first magnetic means coupled to said holder, for applying a uniform magnetic attraction to said holder clamp such that said holder clamp exerts a uniform pressure on said cover slip maintaining a constant separation distance between said slide and said cover slip within said defined volume.

6. The apparatus according to claim 5 wherein said holder clamp is shaped to allow said radiation to pass therethrough.

7. A slide loading apparatus for receiving a slide holding a fluid specimen within a defined region of uniform depth, said specimen being covered by a cover slip, said apparatus comprising
   a holder having a recess for receiving said slide, and an aperture for allowing radiation to pass therethrough,
   a holder clamp, mechanically secured to said holder wherein said holder clamp can be placed in mechanical contact with said cover slip, said holder clamp having an opening therethrough aligned with said aperture in said holder when said holder clamp is in mechanical contact with said cover slip,
   first magnetic means coupled to said holder, for applying a uniform magnetic attraction to said holder clamp such that, when placed in mechanical contact with said cover slip, said holder clamp exerts a uniform pressure on said cover slip to maintain a constant separation distance between said slide and said cover slip over said defined region, and
   a second magnetic means mechanically attached to said holder clamp, for working in concert with said first magnetic means by applying a uniform attractive force against said holder clamp, said second magnetic means for applying an opposite pole attraction to said first magnetic attraction applied by said first magnetic means, ensuring a constant separation distance between said slide and said cover slip.

8. An apparatus for measuring cell concentration in a biological fluid specimen, comprising,
   a slide holding a biological fluid specimen within a defined region of uniform depth,
   a substantially flat cover slip covering said biological fluid specimen,
   a holder having a recess for receiving said slide, and an aperture for allowing radiation to pass therethrough, a holder clamp formed to include magnetically susceptible material, mechanically secured to said holder wherein said holder clamp can be placed in mechanical contact with said cover slip, said holder clamp having an opening therethrough aligned with said aperture in said holder when said holder clamp is in mechanical contact with said cover slip, and first magnetic means coupled to said holder, for applying a uniform magnetic attraction to said holder clamp such that, when placed in mechanical contact with said cover slip, said holder clamp exerts a uniform pressure on said cover slip to maintain a constant separation distance between said slide and said cover slip over said defined region.

* * * * *